United States Patent [19]

Nakamura et al.

[11] Patent Number: 5,071,822
[45] Date of Patent: Dec. 10, 1991

[54] RECORDING MATERIAL

[75] Inventors: Koichi Nakamura, Wakayama; Tadashi Nakamura; Hideki Yanagi, both of Tochigi; Harumasa Yamasaki, Wakayama, all of Japan

[73] Assignee: Kao Corporation, Tokyo, Japan

[21] Appl. No.: 585,262

[22] Filed: Sep. 19, 1990

Related U.S. Application Data

[62] Division of Ser. No. 341,951, Apr. 24, 1989, abandoned.

[30] Foreign Application Priority Data

Apr. 22, 1988 [JP] Japan ................. 63-100898
Nov. 26, 1988 [JP] Japan ................. 1-299027

[51] Int. Cl.$^5$ .............................. B41M 5/30
[52] U.S. Cl. ................... 503/216; 427/150; 503/217; 503/225
[58] Field of Search .............. 427/150; 503/216, 217, 503/225

[56] References Cited

U.S. PATENT DOCUMENTS 4,772,405 9/1988 Wirth ................. 252/47.5

FOREIGN PATENT DOCUMENTS 214932 3/1987 European Pat. Off. .
0338587 10/1989 European Pat. Off. ............ 503/216
61131 6/1974 Japan ................. 568/47
60-28959 2/1985 Japan .
2122784 6/1987 Japan ................. 503/216
2144991 6/1987 Japan ................. 503/216

OTHER PUBLICATIONS

Chemical Absracts 103:71045z (1985).
Chemical Abstracts 103:123141z (1985).

Primary Examiner—Bruce H. Hess
Attorney, Agent, or Firm—Wenderoth, Lind & Ponack

[57] ABSTRACT

Disclosed is a recording material employing an electron donating colorless dye and an electron accepting compound, an improvement being present in that said electron accepting compound is a compound represented by the formula:

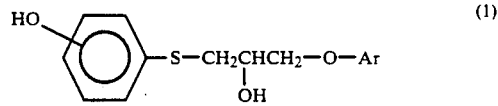

wherein Ar represents a phenyl group, a substituted phenyl group, a benzyl group, a substituted benzyl group, a naphthyl group or a substituted naphthyl group.

4 Claims, No Drawings

RECORDING MATERIAL

This application is a division of now abandoned application Ser. No. 07/341,951 filed on Apr. 24, 1989.

FIELD OF THE INVENTION

The present invention relates to a recording material which employs a color developing reaction of an electron donating colorless dye and an electron accepting compound.

BACKGROUND OF THE INVENTION

Recently, many recording systems have been studied and developed and some of them have been practically used. Among them, heat or pressure sensitive recording materials are widely used for an output of a computer, a printer of an electric calculator, a recorder for medical inspection, a facsimile, an automatic ticket machine, copying and the like, because they do not need complicated treatments for developing, fixing and the like, and can record in a short period of time by a simple and less expensive apparatus without making substantial noise.

The heat or pressure sensitive recording materials work by bringing an electron donating colorless dye into chemical contact with an electron accepting compound to cause color change of the colorless dye. The chemical contact can be carried out by heating using a thermal head, a heat pen, laser beam and the like, or by pressing using a pencil and the like to give a colored image.

As the electron accepting compound (color developer), a compound having a phenolic OH group is generally proposed (Japanese Patent Publications (examined) 9309/1965, 4160/1968, 14039/1970 and 29830/1976, and Japanese Kokai Publication (unexamined) 144193/1981, and the like). Practically employed are bisphenol compounds and 4-hydroxybenzoic acid esters. The color developers require the following properties: (1) to provide images having a high color strength; (2) to provide a stable developed image having no color change by means of moisture, light, oil, time and the like; (3) less water solubility; (4) no subliming properties; (5) producible on an industrial scale and obtainable at a high yield and purity at a low cost; and the like. The above proposed color developers do not meet all requirements For example, some of them do not sharply respond to heat and therefore do not develop desired color strength in case of high speed recording. Others have defects of changing color with time and forming white spots on the developed color image.

In order to overcome the above defects, methods using a sensitizer or a stabilizer are proposed in Japanese Kokai Publications (unexamined) 34842/1974, 106746/1977 and 39139/1978. These methods do not attain desired improvement levels and give rise to other defects of discoloration by oil or other reasons.

SUMMARY OF THE INVENTION

The present invention provides a recording material which sharply responds to heat, and the developed image of which is very stable to surroundings. The recording material of the present invention employs an electron donating colorless dye and an electron accepting compound, wherein the electron accepting compound is a compound represented by the formula:

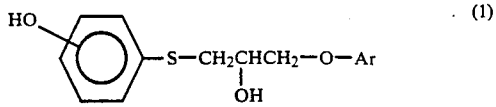

wherein Ar represents a phenyl group, a substituted phenyl group, a benzyl group, a substituted benzyl group, a naphthyl group or a substituted naphthyl group.

In the above mentioned electron accepting compounds (1), some of them are novel. Accordingly, the present invention also provides a phenol compound having the formula:

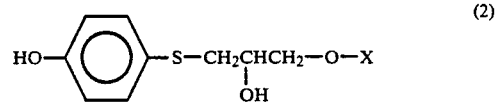

wherein X represents

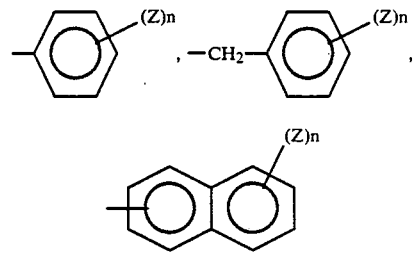

provided that Z represents a substituted or non-substituted alkyl group having 1 to 8 carbon atoms, a cycloalkyl group, an aryl group, an alalkyl group, an alkenyl group, an acyl group, an acyloxy group, an alkoxy group, an aryloxy group, an alkoxycarbonyl group, an aryloxycarbonyl, a hydroxyl group or a halogen atom, n is an integer of 0 to 3; and a process for preparation thereof.

DETAILED DESCRIPTION OF THE INVENTION

The compound (1) preferably has a melting point of at least 50° C., more preferably 70° to 200° C. In the compound (1), Ar can be a phenyl group, a substituted phenyl group, a benzyl group, a substituted benzyl group, a naphthyl group or a substututéd naphthyl group. The substituent includes a linear or branched alkyl group having 1 to 8 carbon atoms, a cycloalkyl group, an aryl group, an aralkyl group, an alkenyl group, an acyl group, an acyloxy group, an alkoxy group, a cycloalkoxy group, an aryloxy group, an alkoxycarbonyl group, a cycloalkoxycarbonyl group, an aryloxycarbonyl group, an amide group and a phenyl group having 1 to 5 substituents selected from a hydroxyl group, a cyano group, a nitro group or a halogen atom. The number of substituents is not limited to one, but may be 2 to 5. The linear or branched alkyl group of the substituent may be further substituted by the above mentioned substituents.

Non-limiting examples of the compound (1) are 1-(4-hydroxyphenylthio)-3-phenoxy-2-propanol, 1-(4-hydroxyphenylthio)-3-(4-hydroxyphenoxy)-2-propanol, 1-(4-hydroxyphenylthio)-3-(3-hydroxyphenoxy)-2-propanol, 1-(4-hydroxyphenylthio)-3-(2-hydroxyphenoxy)-2-propanol, 1-(4-hydroxyphenylthro)-3-(3,4-dihydroxyphenoxy)-2-propanol, 1-(4-hydroxyphenylthio)-3-(2,4-dihydroxyphenoxy)-2-propanol, 1-(4-hydroxyphenylthio)-3-(4-methoxyphenoxy)-2-propanol, 1-(4-hydroxyphenylthio)-3-(3-methoxyphenoxy)-2-propanol, 1-(4-hydroxyphenylthio)-3-(3,4-dimethoxyphenoxy)-2-propanol, 1-(4-hydroxyphenylthio)-3-(3,5-dimethoxyphenoxy)-2-propanol, 1-(4-hydroxyphenylthio)-3-(2,3-dimethoxyphenoxy)-2-propanol, 1-(4-hydroxyphenylthio)-3-(4-ethoxyphenoxy)-2-propanol, 1-(4-hydroxyphenylthio)-3-(3-n-butoxyphenoxy)-2-propanol, 1-(4-hydroxyphenylthio)-3-(4-acetylphenoxy)-2-propanol, 1-(4-hydroxyphenylthio)-3-(3-propionylphenoxy)-2-propanol, 1-(4-hydroxyphenylthio)-3-(4-benzoylphenoxy)-2-propanol, 1-(4-hydroxyphenylthio)-3-(4-acetoxyphenoxy)-2-propanol, 1-(4-hydroxyphenylthio)-3-(3-propionyloxyphenoxy)-2-propanol, 1-(4-hydroxyphenylthio)-3-(4-chlorophenoxy)-2-propanol, 1-(4-hydroxyphenylthio)-3-(3-chlorophenoxy)-2-propanol, 1-(4-hydroxyphenylthio)-3-(2-chlorophenoxy)-2-propanol, 1-(4-hydroxyphenylthio)-3-(2,3-dichlorophenoxy)-2-propanol, 1-(4-hydroxyphenylthio)-3-(2,4-dichlorophenoxy)-2-propanol, 1-(4-hydroxyphenylthio)-3-(2,5-dichlorophenoxy)-2-propanol, 1-(4-hydroxyphenylthio)-3-(2,6-dichlorophenoxy)-2-propanol, 1-(4-hydroxyphenylthio)-3-(3,4-dichlorophenoxy)-2-propanol, 1-(4-hydroxyphenylthio)-3-(3,5-dichlorophenoxy)-2-propanol, 1-(4-hydroxyphenylthio)-3-(4-bromophenoxy)-2-propanol, 1-(4-hydroxyphenylthio)-3-(3-bromophenoxy)-2-propanol, 1-(4-hydroxyphenylthio)-3-(2-bromophenoxy)-2-propanol, 1-(4-hydroxyphenylthio)-3-(2,4-dibromophenoxy)-2-propanol, 1-(4-hydroxyphenylthio)-3-(3,5-dibromophenoxy)-2-propanol, 1-(4-hydroxyphenylthio)-3-(2,3,4-trichlorophenoxy)-2-propanol, 1-(4-hydroxyphenylthio)-3-(2,3,5-trichlorophenoxy)-2-propanol, 1-(4-hydroxyphenylthio)-3-(2,3,6-trichlorophenoxy)-2-propanol, 1-(4-hydroxyphenylthio)-3-(2,4,6-trichlorophenoxy)-2-propanol, 1-(4-hydroxyphenylthio)-3-(2,4,6-tribromophenoxy)-2-propanol, 1-(4-hydroxyphenylthio)-3-(4-nitrophenoxy)-2-propanol, 1-(4-hydroxyphenylthio)-3-(3-nitrophenoxy)-2-propanol, 1-(4-hydroxyphenylthio)-3-(3,4-dinitrophenoxy)-2-propanol, 1-(4-hydroxyphenylthio)-3-(2,4-dinitrophenoxy)-2-propanol, 1-(4-hydroxyphenylthio)-3-(4-methylphenoxy)-2-propanol, 1-(4-hydroxyphenylthio)-3-(3-methylphenoxy)-2-propanol, 1-(4-hydroxyphenylthio)-3-(2-methylphenoxy)-2-propanol, 1-(4-hydroxyphenylthio)-3-(3,4-dimethylphenoxy)-2-propanol, 1-(4-hydroxyphenylthio)-3-(2,4-dimethylphenoxy)-2-propanol, 1-(4-hydroxyphenylthio)-3-(4-t-butylphenoxy)-2-propanol, 1-(4-hydroxyphenylthio)-3-(4-phenoxyphenoxy)-2-propanol, 1-(4-hydroxyphenylthio)-3-(3-phenoxyphenoxy)-2-propanol, 1-(4-hydroxyphenylthio)-3-(4-phenylphenoxy)-2-propanol, 1-(4-hydroxyphenylthio)-3-(3-phenylphenoxy)-2-propanol, 1-(4-hydroxyphenylthio)-3-(3-cyanophenoxy)-2-propanol, 1-(4-hydroxyphenylthio)-3-(2-methoxycarbonylphenoxy)-2-propanol, 1-(4-hydroxyphenylthio)-3-(4-ethoxycarbonylphenoxy)-2-propanol, 1-(4-hydroxyphenylthio)-3-(3,4-dimethoxycarbonylphenoxy)-2-propanol, 1-(3-hydroxyphenylthio)-3-phenoxy-2-propanol, 1-(3-hydroxyphenylthio)-3-(4-hydroxyphenoxy)-2-propanol, 1-(3-hydroxyphenylthio)-3-(4-methoxyphenoxy)-2-propanol, 1-(3-hydroxyphenylthio)-3-(4-ethoxyphenoxy)-2-propanol, 1-(3-hydroxyphenylthio)-3-(4-acetylphenoxy)-2-propanol, 1-(3-hydroxyphenylthio)-3-(4-benzoylphenoxy)-2-propanol, 1-(3-hydroxyphenylthio)-3-(4-chlorophenoxy)-2-propanol, 1-(3-hydroxyphenylthio)-3-(3-chlorophenoxy)-2-propanol, 1-(3-hydroxyphenylthio)-3-(2-chlorophenoxy)-2-propanol, 1-(3-hydroxyphenylthio)-3-(2,3-dichlorophenoxy)-2-propanol, 1-(3-hydroxyphenylthio)-3-(3-bromophenoxy)-2-propanol, 1-(3-hydroxyphenylthio)-3-(2-bromophenoxy)-2-propanol, 1-(3-hydroxyphenylthio)-3-(4-nitrophenoxy)-2-propanol, 1-(3-hydroxyphenylthio)-3-(2,4-dimethylphenoxy)-2-propanol, 1-(3-hydroxyphenylthio)-3-(4-phenylphenoxy)-2-propanol, 1-(4-hydroxyphenylthio)-3-benzyloxy-2-propanol, 1-(4-hydroxyphenylthio)-3-(p-chlorobenzyloxy)-2-propanol, 1-(4-hydroxyphenylthio)-3-(2-naphthyloxy)-2-propanol, 1-(4-hydroxyphenylthio)-3-(1-naphthyloxy)-2-propanol and the like.

Among the above electron accepting compounds (1), there are novel specific phenol compounds having the formula:

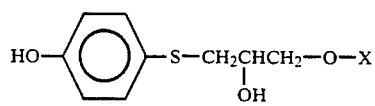

(2)

wherein X represents

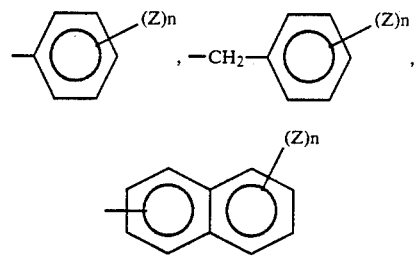

provided that Z represents a substituted or non-substituted alkyl group having 1 to 8 carbon atoms, a cycloalkyl group, an aryl group, an aralkyl group, an alkenyl group, an acyl group, an acyloxy group, an alkoxy group, an aryloxy group, an alkoxycarbonyl group, an aryloxycarbonyl, a hydroxyl group or a halogen atom, and n is an integer of 0 to 3. The novel compound (2) is not only employed as an electron accepting compound for the recording material of this invention, but also has physiological activity, such as antibacterial properties and the like.

The compound (1) can be used alone or in combination as the electron accepting compound of the present invention. It can also be combined with conventional electron accepting compounds, such as bisphenol A, bisphenol S, benzyl 4-hydroxybenzoate and the like.

The compound (1) can be prepared by a reaction of an aryl ether compound having a halohydrin group or a glycidyl group with a suitable thiophenol as follows:

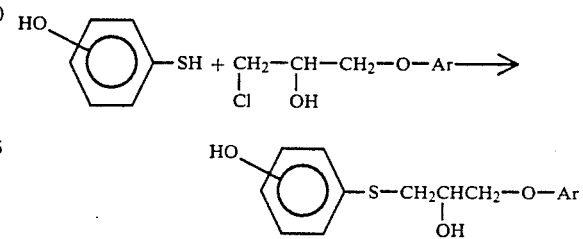

-continued

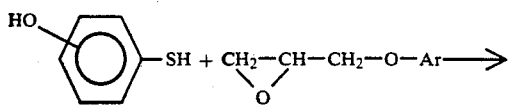

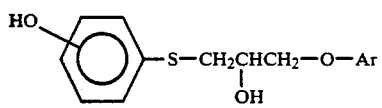

The electron donating dyes employed in the present invention can be leuco dyes, such as triphenylmethanes, fluorans, phenothiazines, auramines, spyropyranes, indolinophthalides, a mixture thereof and the like. More concrete examples of the dyes are 3,3-bis(p-dimerhylaminophenyl)-phthalide, 3,3-bis(p-dimethylaminophenyl)-6-dimethylaminophthalide, 3,3-bis(p-dimethylaminophenyl)-6-diethylaminophthalide, 3,3-bis(p-dimethylaminophenyl)-6-chlorophthalide, 3,3-bis(p-dibutylaminophenyl)-phthalide, 3-cyclohexylamino-6-chlorofluoran, 3-dimethylamino-5,7-dimethylfluoran, 3-diethylamino-7-chlorofluoran, 3-diethylamino-7-methylfluoran, 3-diethylamino-7,8-dibenzfluoran, 3-diethylamino-6-methyl-7-chlorofluoran, 3-(N-p-tolyl-N-ethylamino)-6-methyl-7-anilinofluoran, 3-pyrrolidino-6-methyl-7-anilinofluoran, 2-(N-(3'-trifluoromethylphenyl)amino)-6-diethyl aminofluoran. 2-(3,6- bis(diethylamino)-9-(o-chloroanilino)xantyl lactam benzoate), 3-diethylamino-6-methyl-7-(m-trichloromethylanilino)-fluoran, 3-diethylamino-7-(o-chloroanilino)fluoran, 3-dibutylamino-7-(o-chloroanilino)fluoran, 3-N-methyl-N-amylamino-6-methyl-7-anilinofluoran, 3-N-methyl-N-cyclohexylamino-6-methyl-7-anilinofluoran, 3-diethylamino-6-methyl-7-anilinofluoran, 3-(N,N-diethylamino)-5-methyl-7-(N,N-dibenzylamino)fluoran, benzoyl leucomethylene blue, 6'-chloro-8'-methoxybenzoindolino-pyrirospyran, 6'-bromo-3'-methoxybenzoindolino-pyrirospyran, 3-(2'-hydroxy-4'-dimethylaminophenyl)-3-(2'-methoxy-5'-chlorophenyl)phthalide, 3-(2'-hydroxy-4'-dimethylaminophenyl)-3-(2'-methoxy-5'-nitrophenyl)phthalide, 3-(2'-hydroxy-4'-dimethylaminophenyl)-3-(2'-methoxy-5'-methylphenyl)phthalide, 3-(2'-hydroxy-4'-dimethylaminophenyl)-3-(2'-methoxy-4'-chloro-5'-methylphenyl)phthalide, 3-morpholino-7-(N-propyl-trifluoromethylamilino)fluoran, 3-pyrrolidino-7-trifluoromethylamilinofluoran, 3-diethylamino-5-chloro-7-(N-benzyl-trifluoromethylanilino)fluoran, 3-pyrrolidino-7-(di-p-chlorophenyl)methylanilinofluoran, 3-diethylamino-5-chloro-7-(alpha-phenylethylamino)fluoran, 3-(N-ethyl-p-toluidino)-7-(alpha-phenylethylamino)fluoran, 3-diethylamino-7-(o-methoxycarbophenylamino)fluoran, 3-diethylamino-5-methyl-7-(alpha-phenylethylamino)-fluoran, 3-diethylamino-7-piperidinofluoran, 2-chloro-3-(N-methyltoluidino)-7-(p-n-butylanilino)fluoran, 3-(N-benzyl-N-cyclohexylamino)-5,6benzo-7-alpha-naphthylamino-4'-bromofluoran, 3-diethylamino-6-methyl-7-mesytydino-4,5'-benzofluoran, 3,6-dimethoxyfluoran, 3-p-dimethylaminophenyl)-3-phenylphthalide, 3-di(1-ethyl-2-methylindol)-1-yl-phthalide, 3-diethylamino-6-phenyl-7-azofluoran, 3,3-bis(p-diethyaminophenyl)-6-dimethylamino-phthalide, 2-bis(p-dimethyaminophenyl)methyl-5-dimethyamino-benzoic acid, 3-(p-dimethyaminophenyl)-3-(p-dibenzylaminophenyl)phthalide, 3-(N-ethyl-N-n-amyl)amino-6-methyl-7-anilinofluoran and the like.

The dye and the color developer mentioned above are atomized to several microns in a dispersion medium to form a coating compound. The dispersion medium, for example, is a water-soluble polymer solution having a concentration of about 10% by weight. Examples of water-soluble polymers are polyvinyl alcohol, starch and a derivative thereof, celluloses derivatives (such as methyl cellulose, hydroxyethyl cellulose, carboxymethyl cellulose), synthetic polymers (such as sodium polyacrylate, polyvinyl pyrrolidone, acrylic amide/acrylate copolymer, acrylic amide/acrylate/methacrylic acid copolymer), sodium alginate, casein, gelatin and the like. They can be dispersed by a ball mill, a sand mill, an attritor and the like.

The water-soluble polymer used herein acts as the binder for the heat sensitive paint after coating. In order to impart water resistance, some additives or a polymer emulsion such as a styrene-butadiene latex or an acrylic emulsion can be added to the paint.

The coating solution may further contain various additives. Examples of the additives are inorganic compounds, such as kaolin, talc, calcium carbonate, aluminum hydroxide, magnesium hydroxide, magnesium carbonate, titanium oxide, fine particulate silica and the like to prevent obtains on a recording head. In order to enhance running properties of the head, a fatty acid or metal soap, such as stearic acid, behenic acid, aluminum stearate, zinc stearate, calcium stearate, zinc oleate and the like can also be added.

When the color developer has a high melting point, a thermoplastic material having a low melting point may be formulated into the coating solution to enhance sensitivity to heat. Examples of the thermoplastic materials are wax, such as paraffin wax, microcrystalline wax, polyolefin wax, carnauba wax, Japan wax, bees wax, rice bran wax, higher fatty acid, higher fatty acid ester, higher fatty acid amide and the like. It is preferred that the thermoplastic wax has a melting point of 40° to 120° C. in the practice of the present invention.

The heat sensitive paint containing the above mentioned compounds is coated on a base paper by a blade, an air knife, a roll coater or a gravure method. The coated paper is dried and smoothed to form a heat sensitive recording material of the present invention.

The recording material is suitable for a heat sensitive recording material or a pressure sensitive recording material. The material is also applicable to an electric heat sensitive recording material, a photosensitive recording material, an ultrasonic recording material, an electron beam recording material, an electrostatic recording material, a photosensitive printing plate and the like.

EXAMPLES

The present invention is illustrated by the following examples which, however, are not to be construed as limiting the scope of the invention to their details. In the Examples, part and % are all based on weight.

SYNTHETIC EXAMPLES 1 to 13

(Synthesis of 1-(4-hydroxyphenylthio)-2-propanols)

A toluene solution (10 ml) containing 0.0525 mol of Ar glycidyl ether shown in Table 1 was added dropwise to a toluene solution (50 ml) containing 0.05 mol of 4-hydroxythiophenol in 5 minutes under nitrogen atmosphere with stirring. After stirring for another one hour, the mixture was heated to reflux and continued refluxing for 6.5 hours. The reaction mixture was allowed to cool to room temperature to deposit crystals. The crystals were filtered off and washed with toluene/hexane to obtain a product. The physical properties of the product are shown in Table 1 and NMR data of it is shown in Table 2.

TABLE 1

| Synthetic Examples | Ar | Yield (mole %) | m.p.[1] (°C.) | IR(cm$^{-1}$) (OH)[2] | Elemental analysis (Wt %)[3] | | | |
|---|---|---|---|---|---|---|---|---|
| | | | | | C | H | S | Cl |
| 1 | Phenyl | 94 | 112.4 | 3450 | 65.20 | 6.13 | 11.73 | — |
| | | | | 3250 | 65.19 | 5.84 | 11.61 | — |
| 2 | 4-t-Butylphenyl | 97 | 97.5 | 3480 | 68.90 | 7.00 | 9.60 | — |
| | | | | 3270 | 68.64 | 7.28 | 9.64 | — |
| 3 | 4-Methylphenyl | 94 | 114.8 | 3450 | 66.20 | 6.17 | 10.97 | — |
| | | | | 3220 | 66.18 | 6.25 | 11.04 | — |
| 4 | 2-Methylphenyl | 97 | 61.1 | 3400 | 66.22 | 6.12 | 10.98 | — |
| | | | | 3150 | 66.18 | 6.25 | 11.04 | — |
| 5 | 4-Methoxyphenyl | 96 | 92.0 | 3450 | 62.73 | 5.80 | 10.75 | — |
| | | | | 3225 | 62.73 | 5.92 | 10.46 | — |
| 6 | 4-Chlorophenyl | 92 | 119.2 | 3440 | 57.91 | 4.66 | 10.33 | 11.20 |
| | | | | 3220 | 57.97 | 4.87 | 10.32 | 11.41 |
| 7 | 2-Chlorophenyl | 98 | 70.0 | 3370 | 57.74 | 4.62 | 10.04 | 11.44 |
| | | | | 3150 | 57.97 | 4.87 | 10.32 | 11.41 |
| 8 | 2,4,6-Trichlorophenyl | 82 | 69.3 | 3420 | 47.47 | 3.37 | 8.36 | 28.25 |
| | | | | 3100 | 47.45 | 3.45 | 8.44 | 28.01 |
| 9 | 4-Acetylphenyl | 90 | 104.9 | 3350, 1660 | 64.41 | 5.83 | 10.01 | — |
| | | | | 3250 (C=O) | 65.13 | 5.70 | 10.07 | — |
| 10 | 4-Phenylphenyl | 98 | 133.5 | 3450 | 71.54 | 5.59 | 9.31 | — |
| | | | | 3250 | 71.57 | 5.72 | 9.10 | — |
| 11 | 2-Phenylphenyl | 98 | 71.1 | 3400 | 71.83 | 5.44 | 9.06 | — |
| | | | | 3170 | 71.57 | 5.72 | 9.10 | — |
| 12 | Phenylmethyl | 84 | 90.0 | 3460 | 66.20 | 6.55 | 11.25 | — |
| | | | | 3200 | 66.18 | 6.25 | 11.04 | — |
| 13 | 2-Naphthyl | 72 | 95.3 | 3450 | 69.92 | 5.85 | 9.94 | — |
| | | | | 3200 | 69.91 | 5.56 | 9.82 | — |

[1]Measured by DSC.
[2]KBr
[3]Up is measured value and down is calculated value.

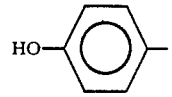

TABLE 2

| Synthetic Examples | HO—⟨◯⟩— | —S—CH$_2$—CH(OH)—CH$_2$—O— | X |
|---|---|---|---|
| 1 | 6.7–7.35(4H, m, Ar—H) | 2.85–3.1(2H, m) <br> 3.85–3.95(1H + 2H, m) | 6.85–7.3(5H, m, Ar—H) |
| 2 | 6.7–7.35(4H, m, Ar—H) <br> 5.25(1H, s, OH) | 2.95–3.15(2H, m) <br> 3.95–4.1(1H + 2H, m) <br> 2.80(1H, s, OH) | 1.29(9H, s, t-Bu) <br> 6.75–7.35(4H, m, Ar—H) |
| 3 | 6.75–7.35(4H, m, Ar—H) | 2.95–3.15(2H, m) <br> 3.95–4.05(1H + 2H, m) <br> 3.33(1H, broad-s, OH) | 2.27(3H, s, Me) <br> 6.75–7.1(4H, m, Ar—H) |
| 4 | 6.7–7.35(4H, m, Ar—H) <br> 5.87(1H, broad-s, OH) | 3.0–3.2(2H, m) <br> 3.95–4.1(1H + 2H, m) | 2.19(3H, s, Me) <br> 6.7–7.2(4H, m, Ar—H) |
| 5 | 6.7–7.35(4H, m, Ar—H) | 2.95–3.15(2H, m) <br> 3.9–4.05(1H + 2H, m) <br> 2.86(1H, s, J=4,2Hz OH) | 3.76(3H, s, OMe) <br> 6.80(4H, s, Ar—H) |
| 6 | 6.75–7.35(4H, m, Ar—H) | 2.95–3.1(2H, m) <br> 3.9–4.05(1H + 2H, m) | 6.75–7.25(4H, m, Ar—H) |
| 7 | 6.7–7.4(4H, m, Ar—H) <br> 5.64(1H, broad-s, OH) | 2.95–3.05(2H, m) <br> 3.85–4.01(1H + 2H, m) <br> 2.96(1H, broad-s, OH) | 6.8–7.4(4H, m, Ar—H) |
| 8 | 6.75–7.35(4H, m, Ar—H) | 3.0–3.2(2H, m) <br> 3.95–4.2(1H + 2H, m) | 7.29(2H, s, Ar—H) |
| 9 | 6.7–7.35(4H, m, Ar—H) | 2.95–3.15(2H, m) <br> 4.0–4.15(1H + 2H, m) <br> 2.90(1H, broad-s, OH) | 2.55(3H, s, Ac) <br> 6.85–7.95(4H, m, Ar—H) |
| 10 | 6.75–7.35(4H, m, Ar—H) | 2.95–3.15(2H, m) <br> 3.95–4.15(1H + 2H, m) | 6.9–7.55(4H, m, Ar—H) <br> 7.25–7.6(5H, m, Ar—H) |
| 11 | 6.6–7.25(4H, m, Ar—H) | 2.8–3.0(2H, m) <br> 3.85–4.1(1H + 2H, m) | 6.9–5.7(9H, m, Ar—H) |
| 12 | 6.75–7.35(4H, m, Ar—H) | 2.85–3.0(2H, m) <br> 3.45–3.6(2H, m) <br> 3.83(1H, m) <br> 3.34(1H, broad-s, OH) | 4.50(2H, s, —CH$_2$—) <br> 7.20–7.4(5H, m, Ar—H) |
| 13 | 6.75–7.35(4H, m, Ar—H) | 3.0–3.2(2H, m) <br> 4.05–4.2(1H + 2H, m) | 7.05–7.8(7H, m, Ar—H) |

EXAMPLE 1

The A and B solutions infra are respectively atomized to an average particle size of not more than 3 microns by a sand mill and 1 part of the A solution was mixed with 3 parts of the B solution to obtain a coating solution. The obtained solution was coated on a high grade paper sheet of 50 g/m² weight in an amount of 6 g/m² solid and then dried, followed by smoothing by a super calender to obtain heat sensitive recording material.

| A Solution | |
|---|---|
| 3-N-methyl-N-cyclohexylamino-6-methyl-7-anilinofluoran | 10 parts |
| 10% Polyvinyl alcohol aqueous solution | 20 parts |
| B Solution | |
| 1-(4-hydroxyphenylthio)-3-phenoxy-2-propanol of Synthetic Example 1 | 10 parts |
| Calcium carbonate | 10 parts |
| 10% Polyvinyl alcohol aqueous solution | 10 parts |

A heat sensitive recording material was prepared as generally described in Example 1, with the exception that 1-(4-hydroxyphenylthio)-3-(4-t-butylphenoxy)-2-propanol of Synthetic Example 2 was employed instead of the product of Synthetic Example 1.

EXAMPLES 3 to 12

The electron accepting compounds shown in Table 3 were employed as the color developer to obtain heat sensitive recording materials as generally described in Example 1. The compound of Examples 4, 7, 8, 9 and 11 were newly prepared as generally described in Synthetic Examples, and the other compounds are already prepared in Synthetic Examples.

TABLE 3

| Examples | Electron accepting compound |
|---|---|
| 3 | 1-(4-hydroxyphenylthio)-3-(4-methylphenoxy)-2-propanol |
| 4 | 1-(4-hydroxyphenylthio)-3-(2, 4-dimethylphenoxy)-2-propanol |
| 5 | 1-(4-hydroxyphenylthio)-3-(4-methoxyphenoxy)-2-propanol |
| 6 | 1-(4-hydroxyphenylthio)-3-(4-chlorophenoxy)-2-propanol |
| 7 | 1-(4-hydroxyphenylthio)-3-(2, 4-dichlorophenoxy)-2-propanol |
| 8 | 1-(4-hydroxyphenylthio)-3-(4-bromophenoxy)-2-propanol |
| 9 | 1-(4-hydroxyphenylthio)-3-(2, 4-dibromophenoxy)-2-propanol |
| 10 | 1-(4-hydroxyphenylthio)-3-(4-phenylphenoxy)-2-propanol |
| 11 | 1-(4-hydroxyphenylthio)-3-(2-methoxycarbonylphenoxy)-2-propanol |
| 12 | 1-(4-hydroxyphenylthio)-3-(4-acetylphenoxy)-2-propanol |

Comparative Example 1

A heat sensitive recording material was prepared as generally described in Example 1 with the exception that benzyl 4-hydroxybenzoate was employed instead of the 2-propanol compound.

COMPARATIVE EXAMPLE 2

The C and D solutions infra were respectively atomized to an average particle size of not more than 3 microns by a sand mill, and then 1 part of the A solution was mixed with 3 parts of the C solution and 5 parts of the D solution to obtain a coating solution. By using the coating solution, a heat sensitive recording material was prepared as generally described in Example 1.

| C Solution | |
|---|---|
| Bisphenol A | 10 parts |
| 10% Polyvinyl alcohol aqueous solution | 20 parts |
| D Solution | |
| Stearamide | 10 parts |
| Calcium carbonate | 10 parts |
| 10% Polyvinyl alcohol aqueous solution | 10 parts |

A heat sensitive recording material was prepared as generally described in Comparative Example 2 with the exception that p-benzylbiphenyl was employed instead of stearamide.

The resultant recording materials were evaluated by color development sensitivity and developed image stability as follows. The result is shown in Table 4.

Color development sensitivity

The heat sensitive materials obtained above were color-developed by a dynamic color-development tester available from Okura Denki K.K. at a printing energy of 0.45 mJ/dot. The color strength was evaluated by a Macbeth RD-918 densitometer available from Macbeth Co., Ltd.

Developed image stability

The color-developed sample was allowed to stand for one month at 25° C. under 60% RH and then the color strength of the developed image was evaluated and its strength retention was calculated.

TABLE 4

| Example number | Color development sensitivity (Color strength) | Developed image stability (Color strength retention rate) |
|---|---|---|
| 1 | 1.49 | 97.2 |
| 2 | 1.43 | 98.2 |
| 3 | 1.43 | 96.8 |
| 4 | 1.35 | 97.9 |
| 5 | 1.48 | 95.8 |
| 6 | 1.46 | 95.1 |
| 7 | 1.34 | 94.8 |
| 8 | 1.47 | 97.6 |
| 9 | 1.46 | 97.0 |
| 10 | 1.38 | 95.3 |
| 11 | 1.33 | 92.5 |
| 12 | 1.40 | 92.5 |
| Comparative Example | | |
| 1 | 1.23 | 62.8 |
| 2 | 1.08 | 82.8 |
| 3 | 1.20 | 70.5 |

As is apparent from the above result, the heat sensitive materials of the present invention have a high color strength even at such a low printing energy as 0.45 mJ/dot. The developed image stability of the present invention is superior to Comparative Examples.

EXAMPLE 13

The compounds of Examples are evaluated as antibacterial agent and the result is shown in Table 5.

I. Test method: agar diffusion method

A test material was dissolved in ethanol to form a solution. 40 μl of the solution was immersed in a paper disk of 8 mm in diameter and dried. The disk was put on SDC agar medium (Nihon Seiyaku Co., Ltd.) coated with a fungi-containing solution ($10^7$/ml) of 0.1 ml and cultured at 30° C. for 2 days. It was evaluated by the width of the inhibition zone which is a transparent area around the disk. The larger the width, the better the antibacterial properties.

II. Test microorganism: gram-positive bacterium

1. *Staphylococcus aureus*
2. *Staphylococcus epidermidis*

III Sample

Four phenol compounds of the present invention. Control compounds is:

1. TCC (Trichlorocarboanilide)
2. MP (Methylparaben)

TABLE 5

| Test micro-organism | Inhibition zone (mm) | | | | | |
|---|---|---|---|---|---|---|
| | Synthetic Examples | | | | Control compound | |
| | 4 | 5 | 7 | 11 | TCC | MP |
| 1 | 4 | 2 | 4 | 3 | 1 | 2 |
| 2 | 2 | 1 | 3 | 2 | 1 | 2 |

The phenol compound of the present invention has superior antibacterial properties in comparison with TCC and MP.

What is claimed is:

1. A recording material comprising a substrate and a coating layer thereon containing an electron donating colorless dye and an electron accepting compound, wherein said electron accepting compound is a compound represented by the formula:

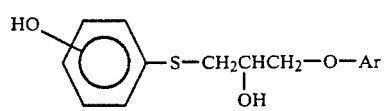

wherein Ar represents a phenyl group, a substituted phenyl group, a benzyl group, a substituted benzyl group, a naphthyl group or a substituted naphthyl group.

2. The recording material according to claim 1 wherein the compound (1) has a melting point of at least 50° C.

3. The recording material according to claim 1 wherein the compound (1) is 1-(4-hydroxyphenylthio)-3-phenoxy-2-propanol, 1-(4-hydroxyphenylthio)-3-(4-t-butylphenoxy)-2-propanol, 1-(4-hydroxyphenylthio)-3-(4-methylphenoxy)-2-propanol, 1-(4-hydroxyphenylthio)-3-(2,4-dimethylphenoxy)-2-propanol, 1-(4-hydroxyphenylthio)-3-(4-methoxyphenoxy)-2-propanol, 1-(4-hydroxyphenylthio)-3-(4-chlorophenoxy)-2-propanol, 1-(4-hydroxyphenylthio)-3-(2,4-dichlorophenoxy)-2-propanol, 1-(4-hydroxphenylthio)-3-(4-bromophenoxy)-2-propanol, 1-(4-hydroxyphenylthio)-3-(2,4-dibromophenoxy)-2-propanol, 1-(4-hydroxyphenylthio)-3-(4-phenylphenoxy)-2-propanol, 1-(4-hydroxyphenylthio)-3-(2-methoxycarbonylphenoxy)-2-propanol or 1-(4-hydroxyphenylthio)-3-(4-acetylphenoxy)-2-propanol.

4. The recording material according to claim 1 wherein the electron donating dye is selected from the group consisting of triphenylmethanes, fluorans, phenothiazines, auramines, spyropyranes and indolinophthalides.

* * * * *